(12) United States Patent
Remigy

(10) Patent No.: US 9,865,428 B2
(45) Date of Patent: Jan. 9, 2018

(54) PREPARATION OF CRYOGENIC SAMPLE FOR CHARGED-PARTICLE MICROSCOPY

(71) Applicant: FEI Company, Hillsboro, OR (US)

(72) Inventor: Herve-William Remigy, Eindhoven (NL)

(73) Assignee: FEI Company, Hillsboro, OR (US)

(*) Notice: Subject to any disclaimer, the term of this patent is extended or adjusted under 35 U.S.C. 154(b) by 0 days.

(21) Appl. No.: 15/218,385

(22) Filed: Jul. 25, 2016

(65) Prior Publication Data

US 2017/0169991 A1     Jun. 15, 2017

(30) Foreign Application Priority Data

Dec. 11, 2015 (EP) .................................. 15199462

(51) Int. Cl.
| | | |
|---|---|---|
| H01J 37/00 | (2006.01) | |
| G01N 1/42 | (2006.01) | |
| H01J 37/26 | (2006.01) | |
| H01J 37/20 | (2006.01) | |
| H01J 37/244 | (2006.01) | |
| F25B 19/00 | (2006.01) | |

(52) U.S. Cl.
CPC ............ *H01J 37/26* (2013.01); *F25B 19/005* (2013.01); *H01J 37/20* (2013.01); *H01J 37/244* (2013.01); *H01J 2237/002* (2013.01)

(58) Field of Classification Search
CPC .. G01N 1/42; H01J 37/20; H01J 37/26; H01J 2237/02
USPC ................ 250/440.11, 441.11, 442.11, 443.1
See application file for complete search history.

(56) References Cited

U.S. PATENT DOCUMENTS

| | | | | |
|---|---|---|---|---|
| 9,116,091 | B2 * | 8/2015 | Remigy .................... | F25D 3/11 |
| 2006/0068373 | A1 * | 3/2006 | Bose ......................... | G01N 1/42 |
| | | | | 435/4 |

| | | | |
|---|---|---|---|
| 2012/0112064 | A1 | 5/2012 | Nagakubo et al. |
| 2012/0255313 | A1 | 10/2012 | Katkov et al. |
| 2013/0205808 | A1 | 8/2013 | Mulders et al. |
| 2014/0069119 | A1 | 3/2014 | Katkov et al. |

(Continued)

FOREIGN PATENT DOCUMENTS

| | | |
|---|---|---|
| EP | 2381236 A1 | 10/2011 |
| EP | 2853847 A1 | 4/2015 |

OTHER PUBLICATIONS

"Electron Microscope", Wikipedia, Retrieved from the Internet Oct. 15, 2015, http://en.wikipedia.org/wiki/Electron_microscope, 11 pages.

"Focused Ion Beam", Wikipedia, Retrieved from the Internet Jul. 11, 2016, https://en.wikipedia.org/wiki/Focused_ion_beam, 7 pages.

"Scanning Electron Microscope", Wikipedia. Retrieved from the Internet Jul. 25, 2016, http://en.wikipedia.org/wiki/Scanning_electron_microscope, 23 pages.

(Continued)

*Primary Examiner* — Nicole Ippolito
(74) *Attorney, Agent, or Firm* — Scheinberg & Associates, P.C.; Michael O. Scheinberg

(57) ABSTRACT

A method of preparing a sample for study in a charged-particle microscope, whereby the sample is subjected to rapid cooling using a cryogen, comprising the following steps:

Providing two conduits for transporting cryogenic fluid, each of which conduits opens out into a mouthpiece, which mouthpieces are arranged to face each other across an intervening gap;

Placing the sample in said gap;

Pumping cryogenic fluid through said conduits so as to concurrently flush from said mouthpieces, thereby suddenly immersing the sample in cryogenic fluid from two opposite sides.

16 Claims, 9 Drawing Sheets

(56) References Cited

U.S. PATENT DOCUMENTS

| | | |
|---|---|---|
| 2014/0248649 A1 | 9/2014 | Mayer et al. |
| 2015/0090878 A1 | 4/2015 | Remigy et al. |
| 2015/0147778 A1* | 5/2015 | Pickard .................... G01N 1/42 |
| | | 435/40.5 |
| 2016/0245732 A1 | 8/2016 | Rémigy |

OTHER PUBLICATIONS

"Scanning Helium Ion Microscope", Wikipedia, Retrieved from the Internet on Jul. 25, 2016, http://en.wikipedia.org/wiki/Scanning_Helium_Ion_Microscope, 2 pages.

"Scanning Transmission Electron Microscopy", Wikipedia, Retrieved from the Internet Jul. 25, 2016, http://en.wikipedia.org/wiki/Scanning_transmission_electron_microscopy, 5 pages.

"Transmission Electron Microscopy", Wikipedia, Retrieved from the Internet Jul. 25, 2016, http://en.wikipedia.org/wiki/Transmission_electron_microscopy, 23 pages.

Adrian, M., et al, "Cryo-negative Staining," Micron, (1998), 16 pages, vol. 29 No. 2/3, Elsevier Science LTD, Great Britain.

Escovitz, W.H. et al., "Scanning Transmission Ion Microscope with a Field Ion Source," Proc. Nat. Acad. Sci. USA, May 1975, pp. 1826-1828, vol. 72, No. 5.

Kasas, S., et al, "Vitrification of cryoelectron microscopy specimens revealed by high-speed photographic imaging", Journal of Microscopy, Jul. 2, 2003, pp. 48-53, vol. 211, Issue 1.

Varentsov, D. et al. "First biological images with high-energy proton microscopy", Physica Medica (2013), pp. 208-213, vol. 29.

\* cited by examiner

PREPARATION OF CRYOGENIC SAMPLE FOR CHARGED-PARTICLE MICROSCOPY

The invention relates to a method of preparing a sample for study in a charged-particle microscope, whereby the sample is subjected to rapid cooling using a cryogen. The invention additionally relates to an apparatus for performing such a method.

The invention also relates to the use of such a sample in a charged-particle microscope, comprising:
- A sample holder, for holding the sample;
- A cooling device, for maintaining the sample at a cryogenic temperature at least while it is on said sample holder;
- A source, for producing a beam of charged particles;
- An illuminator, for directing said beam so as to irradiate the sample;
- A detector, for detecting a flux of radiation emanating from the sample in response to said irradiation.

The term "cryogen" should be interpreted as referring to a liquid at cryogenic temperatures, i.e. at or below −150° C. Examples of such cryogens include liquid ethane, liquid propane, liquid oxygen, and mixtures hereof.

Charged particle microscopy is a well-known and increasingly important technique for imaging microscopic objects, particularly in the form of electron microscopy. Historically, the basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" Focused Ion Beam (FIB), allowing supportive activities such as ion-beam milling or Ion-Beam-Induced Deposition (IBID), for example. More specifically:

- In a SEM, irradiation of a sample by a scanning electron beam precipitates emanation of "auxiliary" radiation from the sample, in the form of secondary electrons, backscattered electrons, X-rays and photoluminescence (infrared, visible and/or ultraviolet photons), for example; one or more components of this flux of emanating radiation is/are then detected and used for image accumulation purposes.
- In a TEM, the electron beam used to irradiate the sample is chosen to be of a high-enough energy to penetrate the sample (which, to this end, will generally be thinner than in the case of a SEM sample); the flux of transmitted electrons emanating from the sample can then be used to create an image. When such a TEM is operated in scanning mode (thus becoming a STEM), the image in question will be accumulated during a scanning motion of the irradiating electron beam.

More information on some of the topics elucidated here can, for example, be gleaned from the following Wikipedia links:
- http://en.wikipedia.org/wiki/Electron_microscope
- http://en.wikipedia.org/wiki/Scanning_electron_microscope
- http://en.wikipedia.org/wiki/Transmission_electron_microscopy
- http://en.wikipedia.org/wiki/Scanning_transmission_electron_microscopy As an alternative to the use of electrons as irradiating beam, charged particle microscopy can also be performed using other species of charged particle. In this respect, the phrase "charged particle" should be broadly interpreted as encompassing electrons, positive ions (e.g. Ga or He ions), negative ions, protons and positrons, for instance. As regards non-electron-based charged particle microscopy, some further information can, for example, be gleaned from sources such as the following:
- https://en.wikipedia.org/wiki/Focused_ion_beam
- http://en.wikipedia.org/wiki/Scanning_Helium_Ion_Microscope—W. H. Escovitz, T. R. Fox and R. Levi-Setti, Scanning Transmission Ion Microscope with a Field Ion Source, Proc. Nat. Acad. Sci. USA 72(5), pp 1826-1828 (1975).
- http://www.ncbi.nlm.nih.gov/pubmed/22472444

It should be noted that, in addition to imaging and performing (localized) surface modification (e.g. milling, etching, deposition, etc.), a charged particle microscope may also have other functionalities, such as performing spectroscopy, examining diffractograms, etc.

In all cases, a Charged Particle Microscope (CPM) will comprise at least the following components:
- A radiation source, such as a Schottky electron source or ion gun.
- An illuminator, which serves to manipulate a "raw" radiation beam from the source and perform upon it certain operations such as focusing, aberration mitigation, cropping (with an aperture), filtering, etc. It will generally comprise one or more (charged-particle) lenses, and may comprise other types of (particle-) optical component also. If desired, the illuminator can be provided with a deflector system that can be invoked to cause its output beam to perform a scanning motion across the sample being investigated.
- A sample holder, on which a sample under investigation can be held and positioned (e.g. tilted, rotated). If desired, this holder can be moved so as to effect the desired scanning motion of the beam w.r.t. the sample. In general, such a sample holder will be connected to a positioning system such as a mechanical stage. The holder may comprise means to maintain the sample in a given (hot or cold) temperature range; in the specific context of the current invention, it will typically comprise means for maintaining the sample at cryogenic temperatures.
- A detector (for detecting radiation emanating from an irradiated sample), which may be unitary or compound/distributed in nature, and which can take many different forms, depending on the radiation being detected. Examples include photodiodes, CMOS detectors, CCD detectors, photovoltaic cells, X-ray detectors (such as Silicon Drift Detectors and Si(Li) detectors), etc. In general, a CPM may comprise several different types of detector, selections of which can be invoked in different situations.

In the particular case of a scanning-type apparatus (such as a SEM or STEM, for example), the CPM will comprise:
- Scanning means, for producing relative scanning motion of the radiation beam and the sample, thereby causing the beam to trace out a pre-determined (two-dimensional) scan pattern on (a presented surface of) the sample. An image is then constructed on the basis of detector output per sampling point on the scan pattern, thus constructing a (two-dimensional) map of said sample (surface). As alluded to above, such scanning means may, for example, be based on beam (scanning) deflection or holder (scanning) motion.

In the case of a transmission-type microscope (such as a (S)TEM, for example), the CPM will also comprise:
- An imaging system, which essentially takes charged particles that are transmitted through a sample (plane) and directs (focuses) them onto analysis apparatus, such as a detection/imaging device, spectroscopic apparatus (such as an EELS module), etc. As with the illuminator referred to above, the imaging system may also perform other functions, such as aberration mitigation, cropping, filtering, etc., and it will generally comprise one or more charged-particle lenses and/or other types of particle-optical components.

In what follows, the invention will—by way of example—often be set forth in the specific context of electron microscopes. However, such simplification is intended solely for clarity/illustrative purposes, and should not be interpreted as limiting.

Biological specimens (such as cells, cell components, single-cellular organisms, etc.) that need to be stored and studied in a body of aqueous liquid (such as water, electrolyte, cell fluid, blood plasma, etc.) can present significant challenges vis-à-vis their examination in a CPM, since:
- An aqueous liquid introduced into a (quasi-)vacuum environment of a CPM will start to outgas/boil, thus tending to degrade the specimen;
- In order to prevent this, a sample (specimen+aqueous liquid) can first be frozen before being introduced into said vacuum;
- However, so as to prevent damage to the specimen caused by the formation of (sharp) ice crystals, such freezing must generally be performed very rapidly, with the aim of achieving sample vitrification (solidification into an amorphous, glass-like phase) without significant ice crystallization.

In order to facilitate such vitrification—but also to allow the sample to be studied in a transmission-type CPM, such as a TEM—the sample should be relatively thin (sheet-like), but one should still be able to support it by its edges (so that the employed means of support have no significant effect on beam penetration). To this end, use if typically made of a grid-like holder (such as a so-called TEM Autogrid®), across which a perforated membrane (such as a so-called "holey carbon film") is spanned, in whose perforations a small quantity of sample can be held (by surface tension effects).

A method as set forth in the opening paragraph above is elucidated in the article *Vitrification of cryoelectron microscopy specimens revealed by high-speed photographic imaging* by S. Kasas et al., J. Microscopy 211(1), July 2003, pp. 48-53. This article is basically interested in studying stroboscopically analyzed, time-resolved thermal contact profiles between a grid-like sample holder (3 mm-diameter copper grid, carbon membrane, aperture size typically 70-200 µm, perforation size ~2 µm, typical pitch of ~1-5 µm between perforations) and a cryogen bath into which it is plunged. In this regard, it discusses the difference between "vertical plunging" of the sample holder into a cryogen (whereby the plane of the sample holder is perpendicular to an exposed surface of the cryogen) and "horizontal plunging" (whereby the plane of the sample holder is parallel to an exposed surface of the cryogen), and it proposes the latter as a way of achieving a more uniform vitrification result than the former (in terms of more homogeneous heat transfer from the sample to the cryogen). However, the article does not (substantially) concern itself with other important aspects of the sample preparation and, in particular, fails to address the subject of sample contamination.

In studies preceding the invention, the inventor noticed that the "horizontal plunging" method alluded to above consistently tended to produce samples that suffered from significant contamination. See, for example, FIG. 2A, which shows a 1 µm×1 µm square portion of a vitrified sample obtained using prior-art techniques. At the employed magnification (~30 k), this square should largely be a quasi-uniform grey color; however, as can clearly be seen from the Figure, the sample is instead covered by a distribution of dark, dot-like features. The presence of these contaminant features can greatly hinder subsequent analysis of the sample in a CPM, since they act as scattering sites for the CPM's imaging beam of charged particles. If a particular study specimen happens to be located along a shared line-of-sight with such a contaminant feature, or proximal thereto, then it generally cannot be satisfactorily viewed using the CPM.

In an attempt to address this problem, the inventor (and collaborators) first examined the contamination phenomenon referred to above, and discovered that it was due to leaching of water out of the interior of the sample and onto its backside as its frontside is plunged into a cryogen bath. As a remedy, the inventor and team introduced a novel technique in U.S. Pat. No. 9,116,091 [FNL1320] (incorporated herein by reference), in which:
- A sample is horizontally plunged into a cryogen bath, frontside first;
- Just before the frontside of the sample contacts the cryogen, a blast of (vapor-phase) cryogenic fluid is administered (from a nozzle) to the backside of the sample.

This technique aims to achieve simultaneous vitrification of the frontside and backside of the sample, in an attempt to impede the "leaching" of contaminants referred to above (by "sealing" the backside before leaching can occur through it).

Although the technique alluded to in the previous paragraph produces a significant improvement compared to the prior-art techniques that pre-dated it, the inventor sought to improve it still further. The results of this endeavor are the subject of the current invention.

It is an object of the invention to provide an improved method of preparing cryogenic samples by vitrification. In particular, it is an object of the invention that such a method should produce more uniform results as compared to prior-art techniques. Specifically, it is an object of the invention that the new method should further reduce the prevalence of unwanted contamination effects in the vitrification process.

These and other objects are achieved in a method as set forth in the opening paragraph above, which method is characterized by the following steps:
- Providing two conduits for transporting cryogenic fluid, each of which conduits opens out into a mouthpiece, which mouthpieces are arranged to face each other across an intervening gap;
- Placing the sample in said gap;
- Pumping cryogenic fluid through said conduits so as to concurrently flush from said mouthpieces, thereby suddenly immersing (dousing, drenching, showering) the sample in cryogenic fluid from two opposite sides.

This novel technique differs from the prior art in a number of significant ways, including the following:
(i) The sample is no longer plunged into a body of liquid cryogen; instead, the cryogen is brought to the sample through said conduits.
(ii) Such a set-up allows complete symmetry as regards the cooling of the sample's backside and frontside: the flush of cryogen from both inventive mouthpieces can be the same in terms of cryogen type, phase, temperature, flow cross-section and flow rate. This contrasts strongly with horizontal plunging techniques in the prior art, in which there are intrinsic differences between the cooling conditions for the sample's frontside and backside; for example, in the abovementioned U.S. Pat. No. 9,116,091, the sample frontside experiences a bath of cryogen whereas the sample backside experiences a spray of cryogen—resulting in frontside/backside differences in heat capacity/heat conductance, exposure geometry/pattern/extent, fluid pressure, phase, etc.

(iii) The sample can be static relative to the conduits when they administer their flush of cryogenic fluid. This is important, since the grids/membranes used for sample mounting are generally quite brittle/fragile, and suddenly moving/plunging them into a stagnant body of liquid can damage them. In the invention, this problem can be mitigated by simultaneously administering a flush of cryogen to opposite faces of a static sample, which tends to produce more symmetric forces on its grid/membrane. As a result, one can often make use of relatively thin grids/membranes, without necessarily having to switch to sturdier ones.

It should be noted that the cryogenic fluid that is flushed from the mouthpieces may be a liquid or a (dry) gas/vapor, as long as it is the same for each mouthpiece. Liquids tend to be preferable over gas-phase fluids, inter alia because of the greater heat capacity of liquids, and the relative ease with which they can be stored and pumped. It should also be noted that, if desired, the mouthpieces may contain a mesh/sieve or other form of flow-path sub-division, e.g. so as to achieve laminar flow and/or a particular flow pattern.

In a set-up according to the present invention, the cryogenic fluid may, for example, be pumped through the employed conduits using one or more electric pumps; these may be switched on/off as required, and/or a valve system can be used to open/close the flow in the conduits at will. However, in an alternative embodiment, use is made of a "manual pumping" set-up in which:

Said conduits are arranged in a plunger, whereby each conduit has an entrance aperture on an underside of the plunger, and said gap is provided as a slot in a topside of the plunger;

A bath of cryogenic fluid is provided beneath said plunger;

Said sample is inserted into said slot using a tool that applies downward pressure on said plunger, thereby at least partially submerging the plunger and causing cryogenic fluid in said bath to flow into said entrance apertures and emerge through said mouthpieces.

Such a set-up is illustrated in FIGS. 3A-3C for example, and it effectively makes use of a fluid displacement mechanism similar to that used in a piston (whereby the plunger plays the role of the piston head [with overflow conduits], and the cryogenic bath is contained in the piston tube). In such an embodiment, it should be noted that:

The "tool" in question may, for example, be a tweezers or pliers, which can be used to grasp the specimen by its edge. Such a tool may, for example, contain a feature such as a protrusion, burl or local enlargement that engages with the top of the plunger (or some structure thereon) in order to convert insertive motion of the tool (in the slot) into (downward) co-motion of the plunger.

The plunger may initially (shallowly) float in the cryogen bath, or may alternatively hang over the bath.

Although the illustrations in FIGS. 3A-3C depict a scenario in which the sample plane is oriented vertically and the cryogenic fluid flushes from the mouthpieces horizontally, this does not necessarily have to be the case. Instead, one could, for example, construct a set-up in which the sample plane is oriented horizontally, the mouthpieces are arranged above and below it, and the cryogenic fluid flushes from the mouthpieces vertically. In both scenarios, it is desirable to have the (cumulative) lengths of both conduits substantially equal, so as to ensure substantially synchronous issuance of cryogenic fluid from both mouthpieces when the plunger is suitably submerged.

The plunger may be made of various materials, as long as they are compatible (e.g. in terms of brittleness) with use at cryogenic temperatures. Examples include stainless steel, titanium and (certain) ceramics, for instance.

Although it is not a restrictive/necessary aspect of the present invention, in the case of many common types of sample, the following will apply:

The sample is substantially planar, with oppositely-located major surfaces;

The sample can be arranged in said gap so that said major surfaces face said mouthpieces.

Such an arrangement basically stipulates the following:

One can associate a terminal/extremal/circumferential perimeter with each of the mouthpieces. This will typically be circular, although this does not necessarily have to be the case.

These perimeters will ideally be centered on a common axis.

This common axis will intersect the plane of the (planar) sample at an (approximately) normal/perpendicular angle.

The common axis will also ideally pass through a geometric center/centroid/barycenter of the sample.

Ideally, the sample will be positioned so that it is equidistant from the mouthpieces (or—in the case of sample comprising a membrane spanned on a grid—so that the membrane is equidistant from the mouthpieces). If the sample/membrane is closer to a first mouthpiece than to the second mouthpiece, then one can still ensure simultaneous flushing of the frontside and backside of the sample by, for example:

Slightly delaying pumping of cryogen into the conduit connected to the first mouthpiece; or/and Embodying the conduit connected to the first mouthpiece to be slightly longer than that connected to the second mouthpiece.

With respect to the cryogen bath into which the sample is plunged, there are various possible choices as regards the cryogen used. For example, various practitioners report using a liquid ethane/propane mix. In a particular embodiment of the invention, the cryogen in the bath comprises liquid ethane (without substantial quantities of other constituents) at a temperature in the range −160° C. to −183° C. When vitrifying a sample by plunge-cooling it, one can tend to adhere to a rule of "the colder the better". However, at temperatures below ca. −183° C., the inventors have observed that liquid ethane tends to become so viscous as to start to impede the plunging process, e.g. by clinging to the sample holder. Temperatures above this level (e.g. −175° C.) are therefore generally preferable.

In order to achieve satisfactory vitrification of the sample, its exposure to cryogenic fluid from the mouthpieces of the current invention should be relatively sudden—hence the term "flush". If exposure to the cryogenic fluid from the mouthpieces is more gradual/extended, then there is a risk that the sample will (at least partially) freeze into crystalline form rather than solidifying amorphously—which is undesirable in the context of the current invention. The timing and duration of the inventive flush can be tuned/optimized in dependence on various factors, such as the thickness of (the grid/membrane of) the sample, the temperature of the employed cryogenic fluid, the pressure/flow pattern produced by the mouthpieces, etc. As a non-binding example, the flush may have a duration of 100 milliseconds or more; in the case of a sample comprising a holey membrane on a grid, a longer duration will generally help to ensure that, in addition to producing vitrification of the aqueous film in the holey membrane, residual heat is removed to a satisfactory extent from the grid (and any associated supporting member), so as to prevent unwanted "reheating" of the membrane by heat leakage from the grid. After vitrification occurs, the aqueous film temperature will preferably remain below about −145° C., to prevent unwanted formation of crystalline ice. The skilled artisan will be able to choose the flush duration, tailored to the set-up and parameters pertaining to a given embodiment of the invention.

The invention will now be elucidated in more detail on the basis of exemplary embodiments and the accompanying schematic drawings, in which.

Figure 3A:
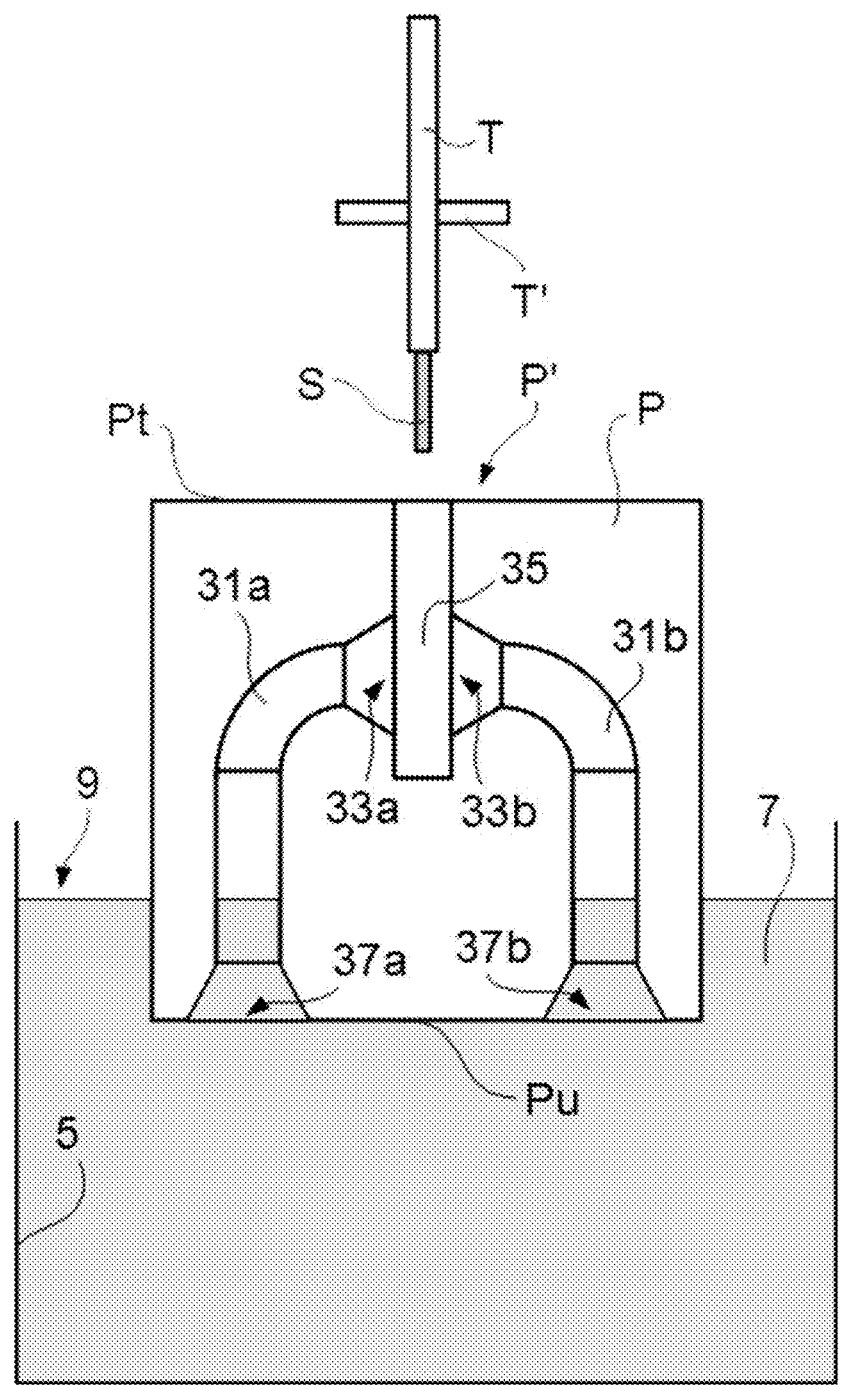
Figure 3B:
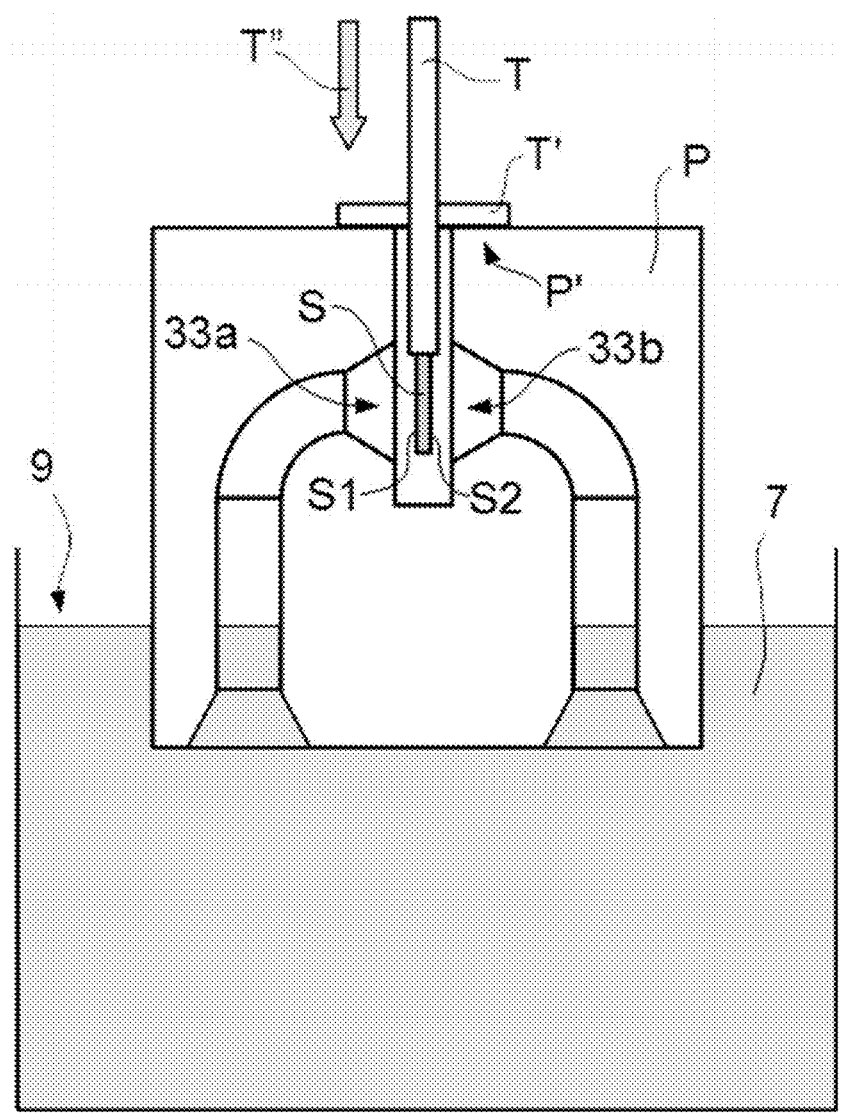
Figure 3C:
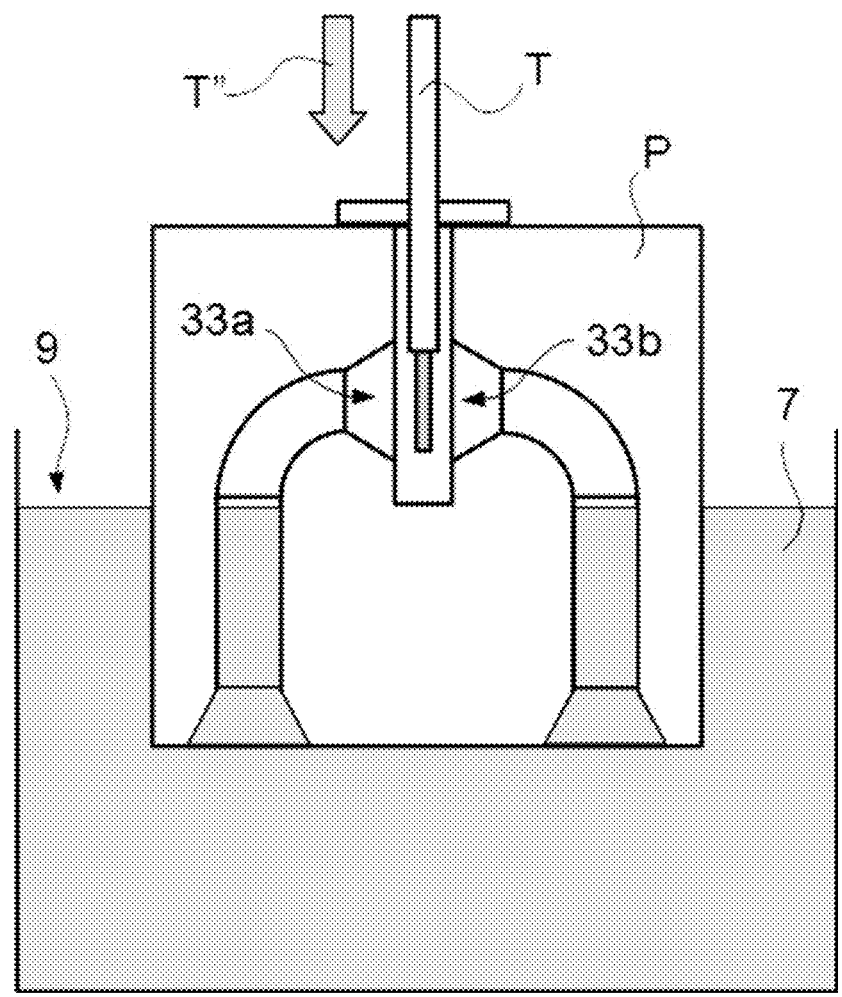

FIGS. 3A-3C render a longitudinal cross-sectional view of aspects of an embodiment of an apparatus according to the present invention (for enacting the inventive method).

Figure 4:
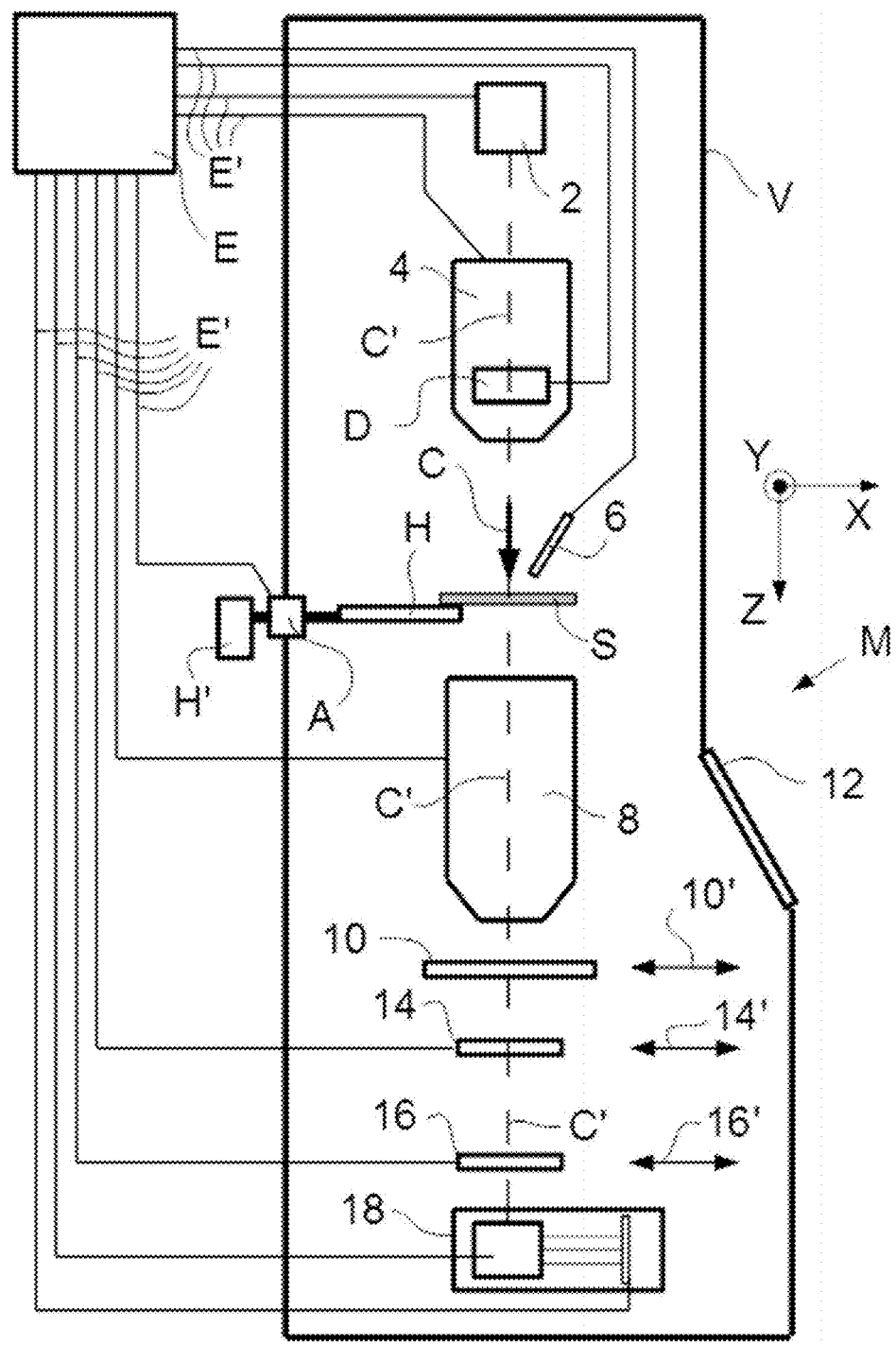

FIG. 4 renders a longitudinal cross-sectional view of a charged-particle microscope that lends itself to use with the current invention.

In the Figures, where pertinent, corresponding parts are indicated using corresponding reference symbols. It should be noted that, in general, the Figures are not to scale.

Comparative Example (Prior Art)

Figure 1A:
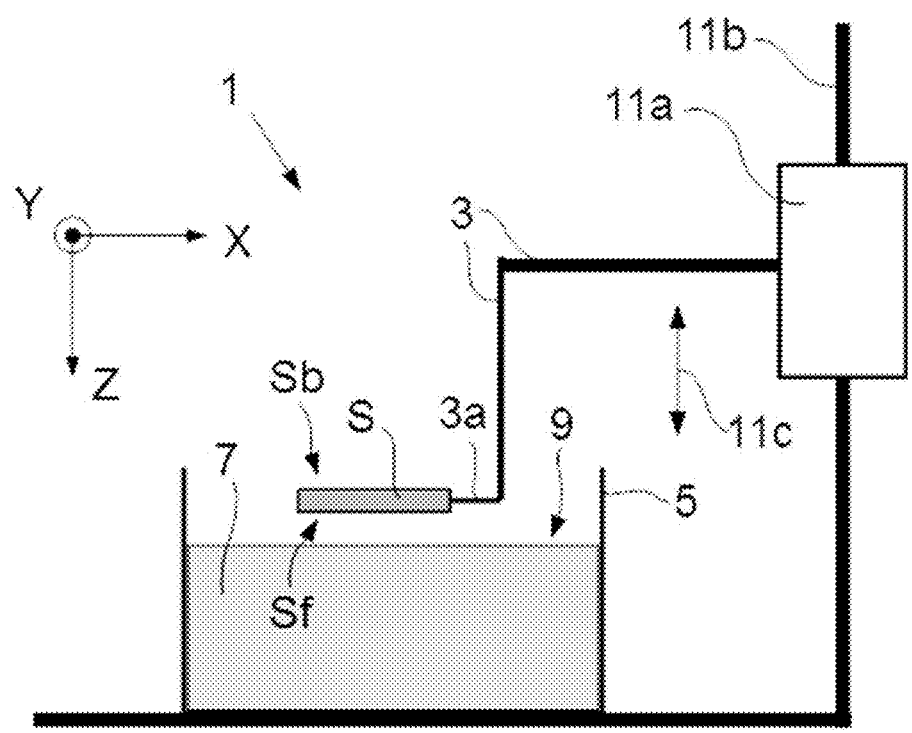
FIGS. 1A-1C depict various prior-art methods for vitrifying a sample.

FIG. 1A renders a schematic elevational view of aspects of a prior-art apparatus 1 for plunge-cooling a sample S to a cryogenic temperature, more specifically using the "horizontal plunging" technique referred to above. The sample S will typically (but not necessarily) have a composite structure of a type such as that shown in more detail in FIG. 1D. Note the Cartesian coordinate system XYZ, which will be used in the following description. The depicted apparatus 1 comprises:

An arm 3 that can be used to grip the sample S at/proximal an edge thereof, and retain the sample S in a substantially horizontal orientation (parallel to the XY plane). This arm 3 comprises a gripper 3a that grips the sample S using, for example, a tweezers action. If desired, the sample S may have a small protruding lug (not depicted) that allows it to be more easily gripped by gripper 3a.

A container 5 (such as a dewar) that can be at least partially filled with a bath of cryogen 7, such that said cryogen 7 has an exposed upper surface 9 (which will be substantially horizontal, apart from relatively small meniscus effects).

A dropping mechanism 11a, 11b that can be used to (at least partially) move the arm 3 into the container 5, allowing a sample S in/on (the gripper 3a of) the arm 3 to be plunged below the cryogen surface 9, with a frontside Sf of the sample S pointing downward (parallel to the Z direction). As here depicted, the dropping mechanism 11a, 11b comprises a slider 11a that can move up and down along a rod 11b (as indicated by the arrows 11c), parallel to the Z direction. The downward motion of the slider 11a during the plunge may, for example, be free-fall, catapulted or motorized. As an alternative/supplement to the depicted mechanism, one could also just manually dip the sample S below the cryogen surface 9.

Figure 1B:
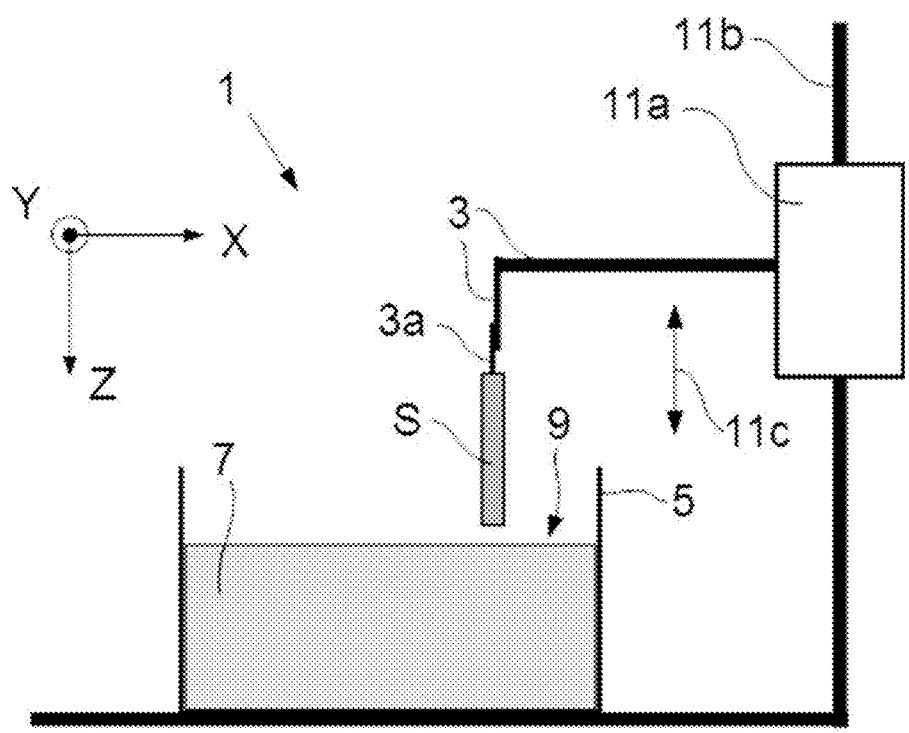
Figure 1C:
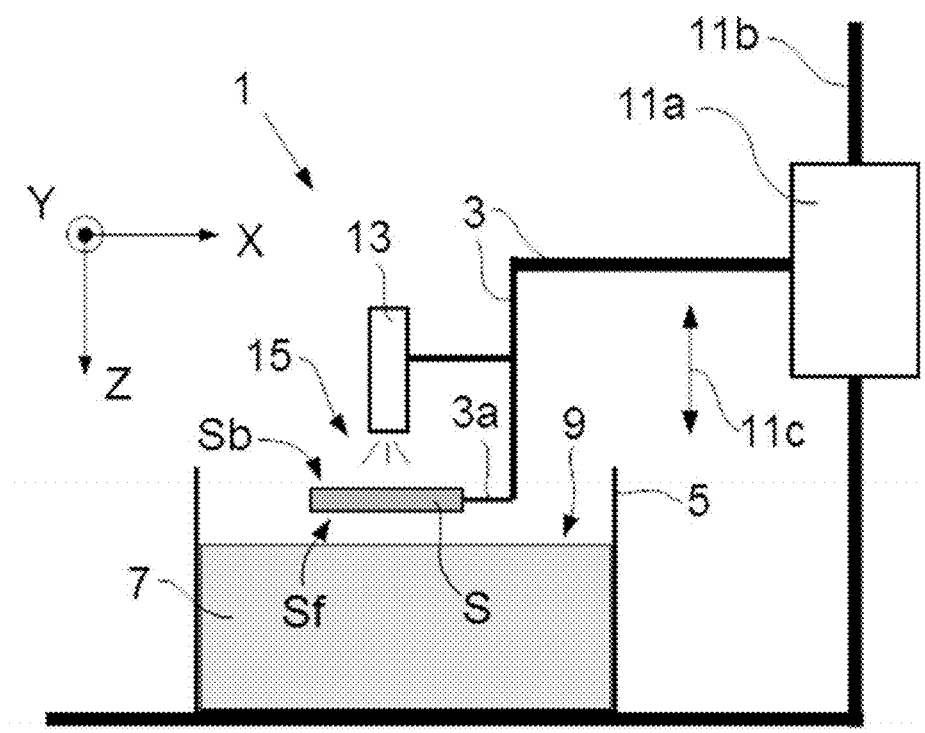
Figure 1D:
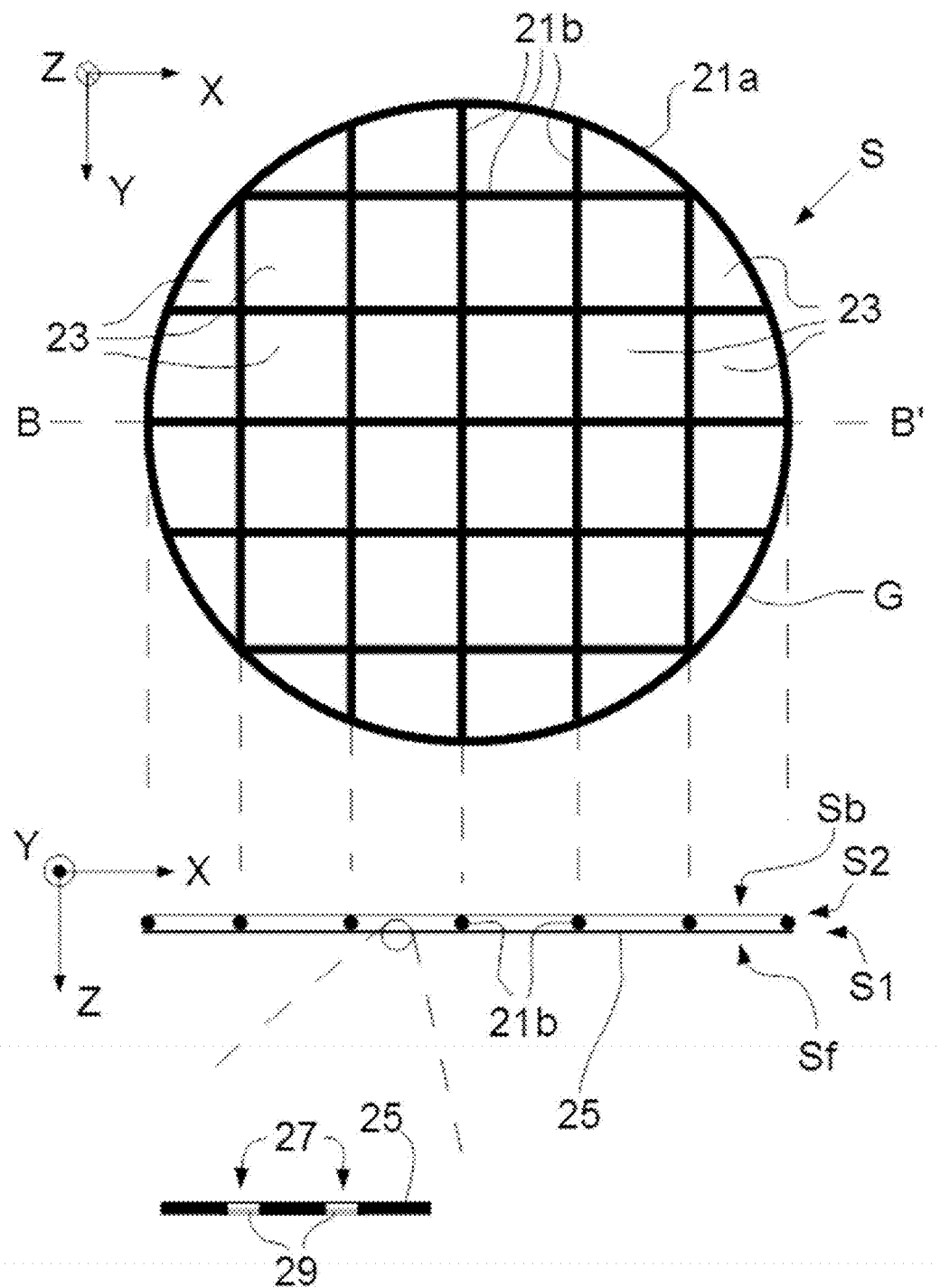
FIG. 1D illustrates (a particular embodiment of) a common sample structure used in vitrification procedures.

FIG. 1D (not to scale) renders more detailed (schematic) views of aspects of a particular embodiment of a sample S that can be used in conjunction with the apparatus 1 of FIG. 1A (and also in the present invention). This particular type of sample S comprises what is often referred to as a "grid" or "Autogrid" G. It comprises a circular ring 21a of Cu wire, the diameter of the ring typically being of the order of about 3 mm and the diameter of the wire typically being of the order of about 50-100 μm. Attached within the ring 21a are straight wire portions 21b, which are (in this case) arranged to form an orthogonal grid pattern, thus defining a matrix-like array of (substantially square) apertures (openings/holes/windows) 23. The middle portion of FIG. 1D shows a transverse cross-sectional view of the upper portion of the Figure, taken along the diameter B-B'. It shows that the grid G has a substantially planar (plate-like) form, with opposed first (S1) and second (S2) "faces" substantially parallel to one another. As here depicted, a membrane 25 has been spanned upon the first face S1 (and, optionally, affixed to the wires 21b, e.g. using an adhesive or by molten bonding). This membrane 25 may, for example, comprise a carbonaceous material such as nylon or graphene, and will typically have a thickness (in the Z direction) ranging from about 0.3 nm to hundreds of nm. The membrane 25 contains a distribution of perforations 27, which are clearly visible in the detailed view at the bottom of the Figure. These perforations 27 typically have a diameter (parallel to the XY plane) of the order of about 2 μm. In essence, the grid G acts as a scaffold for the membrane 25, and the membrane 25 in turn acts as a supporting structure for the perforations 27 (so that it is sometimes referred to as a "holey carbon support"). It is within the perforations 27 that the ultimate "specimen" is to be provided and supported—in the form of a thin film 29 of aqueous liquid (comprising one or more study specimens suspended therein) that is spanned across each given perforation 27, remaining in place (inter alia) by virtue of surface tension effects. It should be noted that structures as depicted in FIG. 1D (grid G+perforated membrane 25, 27) and as described above are commercially available, e.g. from firms such as Ted Pella, Inc., of Redding, Calif., USA. It is also possible to purchase (a variety of) pre-manufactured holey carbon films (corresponding to the perforated membrane 25, 27), e.g. from firms such as Quantifoil Micro Tools GmbH, Jena, Germany.

A film 29 of aqueous liquid can be provided in the various perforations 27 of the membrane 25 using methods well described in technical literature and known to the skilled artisan. In one such known method, a sheet of blotting paper (not depicted) is pressed against the outer/lower surface of membrane 25, is then moistened with the aqueous liquid in question, and is subsequently removed (e.g. peeled off) of the membrane 25—causing (most of) the apertures 27 to be endowed with a (mini-)film 29 of the aqueous liquid, which is spanned within them by surface tension effects. A method of this type is described, for example, in the article Cryo-negative Staining by Marc Adrian et al. in Micron 29 (2-3), Elsevier Science Limited, 1998, pp. 145-160, and will not receive further attention here. Reference is also made to an alternative method that is set forth in European Patent Application EP 15156546.2 [FNL1504] (incorporated herein by reference).

Returning now to FIG. 1A, once the sample S has been provided with its film(s) 29 of aqueous liquid as set forth above, it can be mounted upon the gripper 3a of the arm 3, in such a manner that the membrane 25 faces down toward the cryogen surface 9, thus forming a frontside Sf of the sample S (opposite to a backside Sb). A suitable bath of cryogen 7 (e.g. liquid ethane) is provided in the container 5, and the dropping mechanism 11a, 11b is then used to suddenly plunge the sample S into the cryogen 7, e.g. at a speed of ca. 2 ms$^{-1}$. Such a procedure is, for example, described in the above-mentioned article by Kasas et al. After the sample S has been plunge-cooled in this manner, it is removed from the cryogen 7 and placed on/in a cryo-holder (not depicted) that can maintain it at cryogenic temperature until it undergoes study in a CPM.

Figure 2A:
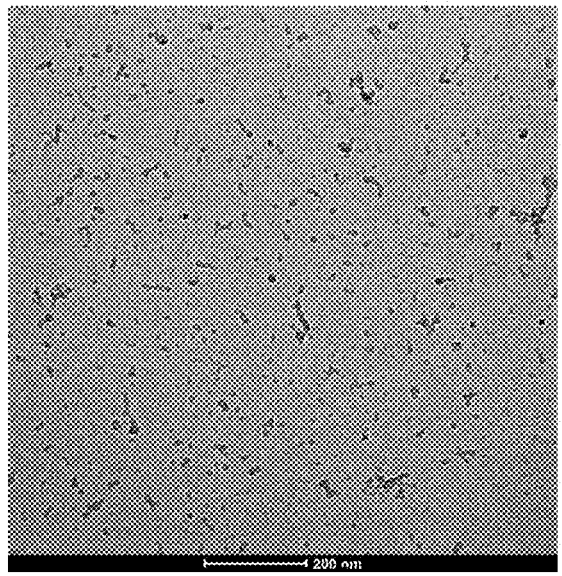
FIGS. 2A and 2B are relatively low-magnification TEM images of aqueous liquid samples prepared on a grid and vitrified using a method according to the prior art (FIG. 2A) and the current invention (FIG. 2B).

As already set forth above, the inventors have found that this prior-art approach yields unsatisfactory results in terms of sample quality. More particularly, samples cooled in this manner tend to demonstrate serious contamination. This effect is shown in FIG. 2A, which depicts a 1 μm×1 μm square portion (tile) of a film 29 of aqueous liquid that has been plunge-cooled using a prior-art apparatus/technique as illustrated in FIG. 1A and set forth above, and that is here imaged using a cryo-TEM at relatively low magnification. What should be a largely homogeneous/featureless image is instead speckled with dark, dot-like features. As explained above, the inventor has established that these features are, in fact, surfacial islands of ice that have formed on the side of the film 29 facing upward/away from the cryogen surface 9 during plunging. The presence of these features obscures study specimens that share a common line-of-sight, and causes unwanted scattering effects in a charged-particle beam used to study the film 29.

For good order, attention is also drawn to the following variants of the situation shown in FIG. 1A and described above:

In FIG. 1B, the sample S is vitrified using a "vertical plunging" technique instead of a "horizontal plunging" approach. Such an approach is discussed in the Kasas reference cited above, and is considered to produce unsatisfactory results, because the sample S is cooled "linearly" (in the vertical direction) rather than "face on".

In FIG. 1C, the method set forth in the abovementioned U.S. Pat. No. 9,116,091 is schematically illustrated. This is once again a "horizontal plunging" technique, but is modified in that a nozzle 13 applies a "puff" 15 of cryogenic vapor to the backside Sb of the sample S as its frontside Sf impacts the cryogen surface 9, in an attempt to achieve simultaneous vitrification of the frontside Sf and backside Sb—unlike the situation of FIG. 1A, where such vitrification is not simultaneous.

Embodiment 1

FIGS. 3A-3C show aspects of an embodiment of a method and apparatus according to the present invention. Starting with FIG. 3A, this shows a pair of conduits 31a, 31b for transporting cryogenic fluid. Each of these conduits 31a, 31b has two external orifices, these being (respectively):

(Lower) entrance orifices 37a, 37b, through which cryogenic fluid can enter the conduits 31a, 31b;
(Upper) mouthpieces (exit orifices) 33a, 33b, through which cryogenic fluid can emerge from the conduits 31a, 31b. These mouthpieces 33a, 33b face each other across an intervening gap 35.

It should be noted that:

For convenience, the various components 31a, 31b, 33a, 33b, 35, 37a, 37b are here depicted as residing in a body P, which may serve as a matrix/structure to keep them in place; for example, body P might be a plug/block of metal or ceramic in which these various components have been created by casting, molding, machining or 3D-printing, for instance. However, this does not necessarily have to be the case, and the various components could instead be (quasi-) free-standing structures.

The orifices 37a, 37b; 33a, 33b are here depicted as being flared, but that does not necessarily have to be the case.

The gap 35 is depicted as being of uniform width, but it could alternatively be tapered, for example.

Also depicted in FIG. 3A is a tool T (such as a tweezers, pincers, pliers, clamp, robot arm, etc.) that can be used to grasp and manipulate a sample S, e.g. by gripping it along its edge. This tool T can be used to position sample S in the gap 35 and between the mouthpieces 33a, 33b.

As already set forth above, one way to supply cryogenic fluid to the entrance orifices 37a, 37b is to simply connect them to (an electrical) cryogen pump (and associated cryogen reservoir) using suitable tubing/piping; one can then pump cryogen through the conduits 31a, 31b and out of the mouthpieces 33a, 33b so as to flush/shower (a sample S located in) the gap 35 with cryogenic fluid. However, in the current embodiment, use is instead made of a (manual) piston action to move cryogenic fluid through the conduits 31a, 31b. To this end, the body P is embodied as a plunger, which has an underside Pu (in which the entrance orifices 37a, 37b are located) and a topside Pt (through which it is possible to access gap 35). This plunger P can then, for example, be (partially) plunged/dipped into a container (tube, vessel) 5 of cryogen 7; as the plunger's underside Pu moves beneath the surface 9, cryogen 7 will be (progressively) forced through the entrance orifices 37a, 37b, though the conduits 31a, 31b and out of the mouthpieces 33a, 33b (see the progression from FIG. 3A to 3B to 3C, which illustrate part of this motion). It should be noted that some degree of capillary action will typically cause some amount of the cryogen 7 to creep up into the conduits 31a, 31b—the extent of such creep depending inter alia on the diameter of the conduits 31a, 31b, the density/viscosity of the cryogen 7, etc.; for simplicity, this effect has not been illustrated in FIGS. 3A-3C.

To produce such plunging motion, the depicted set-up uses the tool T to apply downward force to the plunger P—although this does not necessarily have to be the case, and one could instead push the plunger P downward by other means. As shown in FIGS. 3B and 3C, the tool T has a protrusion/lug T' that engages with a reciprocal area/part P' of the topside Pt of plunger P, allowing downward force on tool T to transfer downward momentum to plunger P: see the illustrative downward arrow T" in FIGS. 3B, 3C. Moreover, the protrusion T' can (if so desired) be exploited to ensure that the sample S is inserted to an optimal depth in gap 35 (ideally substantially symmetrically between mouthpieces 33a, 33b) and can also be used to provide correct lateral positioning of the sample S in the gap 35 (once again, ideally with the (vitreous film of the) sample equidistant from mouthpieces 33a, 33b).

In a non-limiting example of a set-up such as that depicted here, the following illustrative (and approximate) values may apply:

Sample S comprises a planar grid of diameter 3 mm and thickness 0.4 mm.

Diameter of mouthpieces 33a, 33b: 3-4 mm.

Diameter of conduits 31a, 31b: 2.5 mm.

Separation of mouthpieces 31a, 31b/width of gap 35: 1 mm.

Flow rate from mouthpieces 31a, 31b: ~5-15 m/s.

The skilled artisan will be able to tailor his own values to the requirements of a given situation.

Figure 2B:
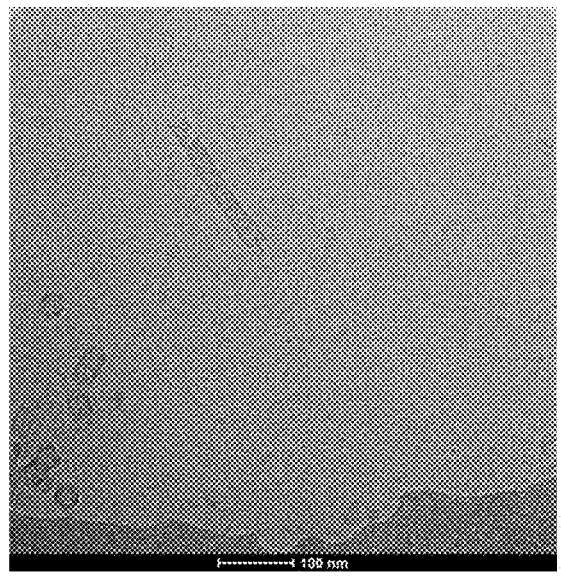

The improved results of the current invention vis-à-vis the prior art are evident from FIG. 2B, in which the contaminant dot-like features of FIG. 2A are entirely absent. The tube-like "floating entities" at the lower left and center of FIG. 2B are Keyhole Limpet Hemocynanin protein complexes, which are not visible in FIG. 2A. The dark region along the base of FIG. 2B is the edge of (a 2 μm-wide aperture in) the employed holey carbon film.

Embodiment 2

FIG. 4 is a highly schematic depiction of an embodiment of a CPM which can be used to examine a sample prepared in accordance with the present invention; more specifically, it shows an embodiment of a transmission-type microscope M, which, in this case, is a TEM/STEM (though, in the context of the current invention, it could just as validly be an ion-based microscope, for example). In the Figure, within a vacuum enclosure V, an electron source 2 (such as a Schottky emitter, for example) produces a beam (C) of electrons that traverse an electron-optical illuminator 4, serving to direct/focus them onto a chosen part of a specimen S (which may, for example, be (locally) thinned/planarized). This illuminator 4 has an electron-optical axis C', and will generally comprise a variety of electrostatic/magnetic lenses, (scan) deflector(s) D, correctors (such as stigmators), etc.; typically, it can also comprise a condenser system (the whole of item 4 is sometimes referred to as "a condenser system").

The specimen S is held on a specimen holder H that can be positioned in multiple degrees of freedom by a positioning system/stage A; for example, the specimen holder H may comprise a finger that can be moved (inter alia) in the XY plane (see the depicted Cartesian coordinate system; typically, motion parallel to Z and (at least) tilt about X/Y will also be possible). Such movement allows different parts of the specimen S to be irradiated/imaged/inspected by the electron beam traveling along axis C' (in the Z direction) (and/or allows scanning motion to be performed, as an alternative to beam scanning). A cooling device H' is in intimate thermal contact with the specimen holder H, and is capable of maintaining the latter at cryogenic temperatures, e.g. using a vat of cryogenic coolant to achieve and maintain a desired low temperature.

The (focused) electron beam C traveling along axis C' will interact with the specimen S in such a manner as to cause various types of "stimulated" radiation to emanate from the specimen S, including (for example) secondary electrons, backscattered electrons, X-rays and optical radiation (cathodoluminescence). If desired, one or more of these radiation types can be detected with the aid of analysis device 6, which might be a combined scintillator/photomultiplier or EDX (Energy-Dispersive X-Ray Spectroscopy) module, for instance; in such a case, an image could be constructed using basically the same principle as in a SEM. However, alternatively or supplementally, one can study electrons that traverse (pass through) the specimen S, emerge (emanate) from it and continue to propagate (substantially, though generally with some deflection/scattering) along axis C'. Such a transmitted electron flux enters an imaging system (combined objective/projection lens) 8, which will generally comprise a variety of electrostatic/magnetic lenses, deflectors, correctors (such as stigmators), etc. In normal (non-scanning) TEM mode, this imaging system 8 can focus the transmitted electron flux onto a fluorescent screen 10, which, if desired, can be retracted/withdrawn (as schematically indicated by arrows 10') so as to get it out of the way of axis C'. An image (or diffractogram) of (part of) the specimen S will be formed by imaging system 8 on screen 10, and this may be viewed through viewing port 12 located in a suitable part of a wall of enclosure V. The retraction mechanism for screen 10 may, for example, be mechanical and/or electrical in nature, and is not depicted here.

As an alternative to viewing an image on screen 10, one can instead make use of the fact that the depth of focus of the electron flux emerging from imaging system 8 is generally quite large (e.g. of the order of 1 meter). Consequently, various other types of analysis apparatus can be used downstream of screen 10, such as:

TEM camera 14. At camera 14, the electron flux can form a static image (or diffractogram) that can be processed by controller E and displayed on a display device (not depicted), such as a flat panel display, for example. When not required, camera 14 can be retracted/withdrawn (as schematically indicated by arrows 14') so as to get it out of the way of axis C'.

STEM imager (camera) 16. An output from imager 16 can be recorded as a function of (X,Y) scanning position of the beam C on the specimen S, and an image can be constructed that is a "map" of output from imager 16 as a function of X,Y. Imager 16 can, for example, comprise a single pixel with a diameter of e.g. 20 mm, as opposed to the matrix of pixels characteristically present in camera 14. Moreover, imager 16 will generally have a much higher acquisition rate (e.g. $10^6$ points per second) than camera 14 (e.g. $10^2$ images per second). Once again, when not required, imager 16 can be retracted/withdrawn (as schematically indicated by arrows 16') so as to get it out of the way of axis C' (although such retraction would not be a necessity in the case of a donut-shaped annular dark field imager 16, for example; in such an imager, a central hole would allow beam passage when the imager was not in use).

As an alternative to imaging using camera 14 or imager 16, one can also invoke spectroscopic apparatus 18, which could be an EELS module, for example (EELS=Electron Energy-Loss Spectroscopy).

It should be noted that the order/location of items 14, 16 and 18 is not strict, and many possible variations are conceivable. For example, spectroscopic apparatus 18 can also be integrated into the imaging system 8.

Note that the controller (computer processor) E is connected to various illustrated components via control lines (buses) E'. This controller E can provide a variety of functions, such as synchronizing actions, providing setpoints, processing signals, performing calculations, and displaying messages/information on a display device (not depicted). Needless to say, the (schematically depicted) controller E may be (partially) inside or outside the enclosure V, and may have a unitary or composite structure, as desired. The skilled artisan will understand that the interior of the enclosure V does not have to be kept at a strict vacuum; for example, in a so-called "Environmental TEM/STEM", a background atmosphere of a given gas is deliberately introduced/maintained within the enclosure V. The skilled artisan will also understand that, in practice, it may be advantageous to confine the volume of enclosure V so that, where possible, it essentially hugs the axis C', taking the form of a small tube (e.g. of the order of 1 cm in diameter) through which the employed electron beam passes, but widening out to accommodate structures such as the source 2, specimen holder H, screen 10, camera 14, imager 16, spectroscopic apparatus 18, etc.

The specimen S shown in FIG. 4 can, for example, be a specimen that has undergone a vitrification procedure according to the present invention. Such a specimen can be maintained at cryogenic temperatures while it is in the CPM M (and also while it is being transported/stored) thanks to the cooling device H'. To this end, one can, for example, employ an embodiment such as the following:

The cooling device H' comprises a dewar/flask that is intimately thermally connected (e.g. via a copper rod and/or braid) to holder H, and that can be filled with a cryogen.

The composite structure H+H' can be inserted into/removed from the CPM M, whereby it can be seated into/clamped by a receiver portion of positioning system A.

Refer, for example, to the set-up discussed in United States Patent Application US 2012/0112064 A1, and similar such set-ups.

The invention claimed is:

1. A method of preparing a sample for study in a charged-particle microscope, whereby the sample is subjected to rapid cooling using a cryogen, comprising:
providing two conduits for transporting cryogenic fluid, each of which conduits opens out into a mouthpiece, which mouthpieces are arranged to face each other across an intervening gap;
placing the sample in said gap; and
pumping cryogenic fluid through said conduits so as to concurrently flush from said mouthpieces, thereby suddenly immersing the sample in cryogenic fluid from two opposite sides.

2. A method according to claim 1, wherein:
said conduits are arranged in a plunger, whereby each conduit has an entrance aperture on an underside of the plunger, and said gap is provided as a slot in a topside of the plunger;
a bath of cryogenic fluid is provided beneath said plunger; and
said sample is inserted into said slot using a tool that applies downward pressure on said plunger, thereby at least partially submerging the plunger and causing cryogenic fluid in said bath to flow into said entrance apertures and emerge through said mouthpieces.

3. A method according to claim 2, wherein:
said sample is substantially planar, with oppositely-located major surfaces; and
the sample is arranged in said gap so that said major surfaces face said mouthpieces.

4. A method according to claim 2, wherein said cryogenic fluid comprises liquid ethane at a temperature in the range −160° C. to −183° C.

5. The method of claim 2, further comprising:
providing a sample in sample holder, within a charged particle microscope;
maintaining the sample at a cryogenic temperature using a cooling device, at least while the sample is on the sample holder;
producing a beam of charged particles from a source;
directing said beam so as to irradiate the sample using an illuminator; and
detecting a flux of radiation using a detector, the radiation emanating from the sample in response to said irradiation.

6. A method according to claim 1, wherein:
said sample is substantially planar, with oppositely-located major surfaces; and
the sample is arranged in said gap so that said major surfaces face said mouthpieces.

7. A method according to claim 6, wherein said sample comprises a planar grid.

8. A method according to claim 7, wherein said cryogenic fluid comprises liquid ethane at a temperature in the range −160° C. to −183° C.

9. The method of claim 7, further comprising:
providing a sample in sample holder, within a charged particle microscope;
maintaining the sample at a cryogenic temperature using a cooling device, at least while the sample is on the sample holder;
producing a beam of charged particles from a source;
directing said beam so as to irradiate the sample using an illuminator; and
detecting a flux of radiation using a detector, the radiation emanating from the sample in response to said irradiation.

10. A method according to claim 6, wherein said cryogenic fluid comprises liquid ethane at a temperature in the range −160° C. to −183° C.

11. The method of claim 6, further comprising:
providing a sample in sample holder, within a charged particle microscope;
maintaining the sample at a cryogenic temperature using a cooling device, at least while the sample is on the sample holder;
producing a beam of charged particles from a source;
directing said beam so as to irradiate the sample using an illuminator; and
detecting a flux of radiation using a detector, the radiation emanating from the sample in response to said irradiation.

12. A method according to claim 1, wherein said cryogenic fluid comprises liquid ethane at a temperature in the range −160° C. to −183° C.

13. The method of claim 12, further comprising:
providing a sample in sample holder, within a charged particle microscope;
maintaining the sample at a cryogenic temperature using a cooling device, at least while the sample is on the sample holder;
producing a beam of charged particles from a source;
directing said beam so as to irradiate the sample using an illuminator; and
detecting a flux of radiation using a detector, the radiation emanating from the sample in response to said irradiation.

14. Use of a sample prepared using a method as claimed in claim 1 in a charged-particle microscope comprising:
a sample holder, for holding the sample;
a cooling device, for maintaining the sample at a cryogenic temperature at least while it is on said sample holder;
a source, for producing a beam of charged particles;
an illuminator, for directing said beam so as to irradiate the sample; and a detector, for detecting a flux of radiation emanating from the sample in response to said irradiation.

15. An apparatus for preparing a sample for study in a charged-particle microscope, whereby the sample is subjected to rapid cooling using a cryogen, comprising:
- a pair of conduits for transporting cryogenic fluid, each of which conduits opens out into a mouthpiece, which mouthpieces are arranged to face each other across an intervening gap in which the sample can be arranged; and
- a pumping mechanism, for pumping cryogenic fluid through said conduits so as to concurrently flush from said mouthpieces and suddenly immerse the sample in cryogenic fluid from two opposite sides.

16. An apparatus according to claim 15, wherein:
said conduits are arranged in a plunger, whereby each conduit has an entrance aperture on an underside of the plunger, and said gap is provided as a slot in a topside of the plunger.

* * * * *